(12) United States Patent
Oishi

(10) Patent No.: US 11,666,297 B2
(45) Date of Patent: Jun. 6, 2023

(54) MEDICAL SYSTEM, MEDICAL IMAGE DIAGNOSIS APPARATUS AND TERMINAL DEVICE

(71) Applicant: CANON MEDICAL SYSTEMS CORPORATION, Otawara (JP)

(72) Inventor: Keisuke Oishi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 125 days.

(21) Appl. No.: 17/126,452

(22) Filed: Dec. 18, 2020

(65) Prior Publication Data

US 2021/0186449 A1 Jun. 24, 2021

(30) Foreign Application Priority Data

Dec. 20, 2019 (JP) .............................. JP2019-229960

(51) Int. Cl.
*G16H 30/40* (2018.01)
*A61B 6/00* (2006.01)
*A61B 6/04* (2006.01)

(52) U.S. Cl.
CPC .......... *A61B 6/5205* (2013.01); *A61B 6/0407* (2013.01); *A61B 6/461* (2013.01); *A61B 6/563* (2013.01)

(58) Field of Classification Search
CPC ........ G16H 30/40; G16H 50/20; G16H 50/70; G16H 15/00; G16H 10/60; A61B 6/032; A61B 5/0022; A61B 6/5294; A61B 8/54; A61B 8/565; A61B 6/5211; A61B 6/03
See application file for complete search history.

(56) References Cited

U.S. PATENT DOCUMENTS

| | | |
|---|---|---|
| 2007/0004980 A1 | 1/2007 | Warner et al. |
| 2013/0208955 A1 | 8/2013 | Zhao et al. |
| 2014/0153808 A1 | 6/2014 | Wu et al. |
| 2016/0335395 A1 | 11/2016 | Wu et al. |
| 2019/0027244 A1 | 1/2019 | Wu et al. |
| 2019/0392944 A1* | 12/2019 | Samset .................. G16H 30/40 |

FOREIGN PATENT DOCUMENTS

| | | | |
|---|---|---|---|
| JP | 2001-306315 A | | 11/2001 |
| JP | 2002-109055 A | | 4/2002 |
| JP | 2005-207857 A | | 8/2005 |
| JP | 2006-508760 A | | 3/2006 |
| JP | 2010-282656 A | | 12/2010 |
| JP | 2014153920 A | * | 8/2014 |
| JP | 2017-107554 A | | 6/2017 |

* cited by examiner

*Primary Examiner* — Don K Wong
(74) *Attorney, Agent, or Firm* — Oblon, McClelland, Maier & Neustadt, L.L.P.

(57) ABSTRACT

A medical system according to an embodiment is a system in which at least one medical image diagnosis apparatus and a server are connected via a network and the medical system includes a storage circuit, a processing circuit, and a display circuit. The storage circuit stores information on examinations that are performed by the at least one medical image diagnosis apparatus. The processing circuit generates proposal information based on information on the examinations. The display circuit displays the proposal information.

16 Claims, 8 Drawing Sheets

MEDICAL SYSTEM, MEDICAL IMAGE DIAGNOSIS APPARATUS AND TERMINAL DEVICE

CROSS-REFERENCE TO RELATED APPLICATIONS

This application is based upon and claims the benefit of priority from Japanese Patent Application No. 2019-229960, filed on Dec. 20, 2019; the entire contents of which are incorporated herein by reference.

FIELD

Embodiments described herein relate generally to a medical system, a medical image diagnosis apparatus and a terminal device.

BACKGROUND

A medical image diagnosis apparatus represented by an X-ray computed tomography imaging device ("X-ray CT apparatus") has various options of hardware, such as an X-ray tube, and software, such as an analysis application specialized in a region to be diagnosed. In general, what option to add to the medical image diagnosis apparatus is determined by negotiation between the side of manufactures and distributers and the side of users.

In the negotiation, however, what option to introduce is often discussed based on the subjective views of the users. Accordingly, options to be introduced do not necessarily reflect the content of actual examinations and usage.

DETAILED DESCRIPTION

A medical system according to an embodiment is a system in which at least one medical image diagnosis apparatus and a server are connected via a network and the medical system includes a storage circuit, a processing circuit, and a display circuit. The storage circuit stores information on examinations that are performed by the at least one medical image diagnosis apparatus. The processing circuit generates proposal information based on the information on examinations. The display circuit displays the proposal information.

With reference to the accompanying drawings, the medical system, a medical information management apparatus, and a terminal device according to the embodiment will be described in detail below.

First Embodiment

Figure 1:
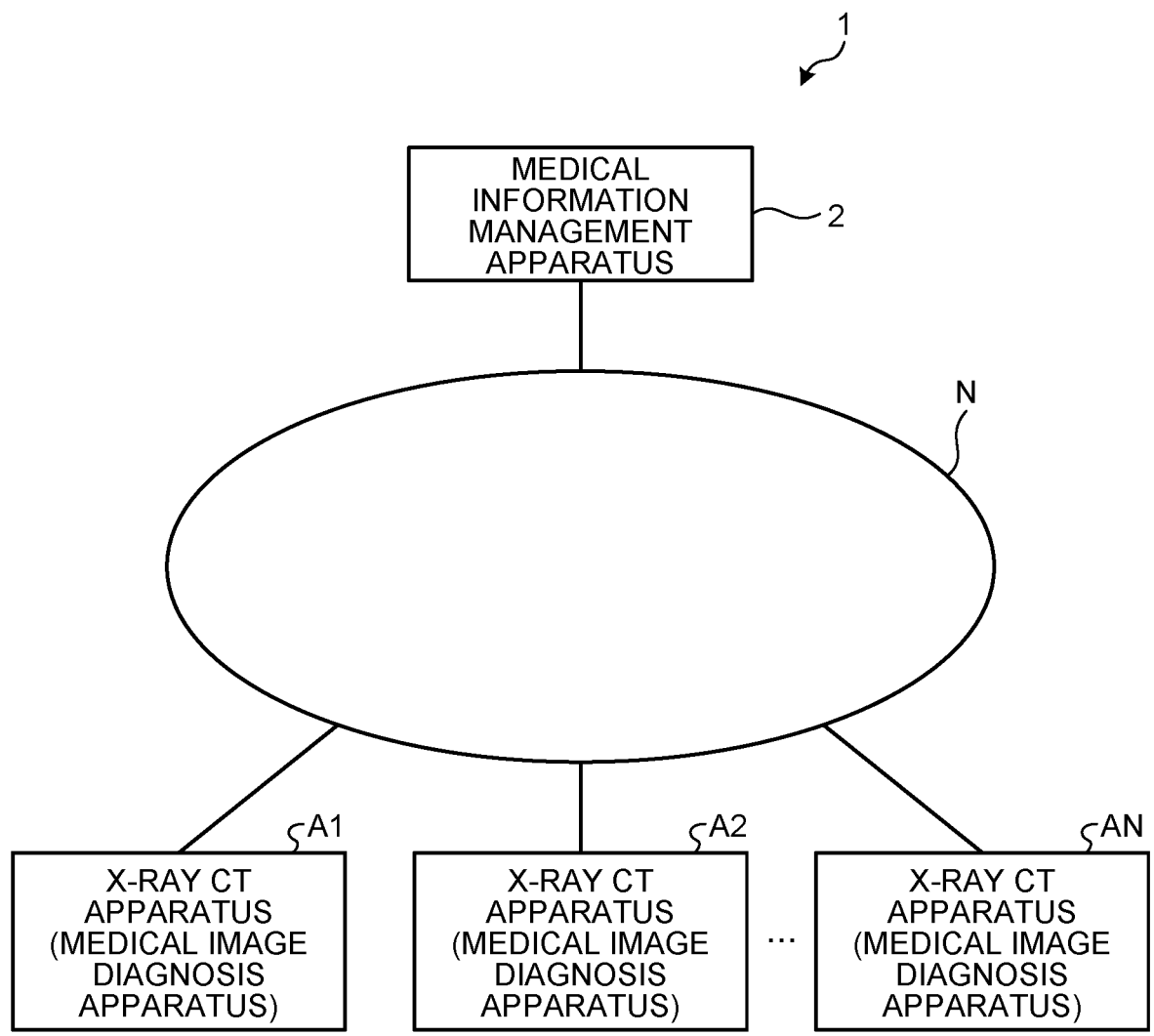
FIG. 1 is a diagram illustrating an example of a configuration of a medical system 1 according to a first embodiment.

FIG. 1 is a diagram illustrating a configuration of a medical system 1 according to a first embodiment. As illustrated in FIG. 1, FIG. 1 is a diagram illustrating the medical system 1 including a medical information management apparatus 2 and a plurality of medical image diagnosis apparatuses A1 to AN. The medical information management apparatus 2 and X-ray CT apparatuses A1 to AN are able to communicate with each another via a network N.

In the first embodiment, for specific description, the case where the medical image diagnosis apparatuses A1 to AN are the X-ray CT apparatuses A1 to AN is exemplified. The medical image diagnosis apparatuses A1 to AN are however not limited to X-ray CT apparatuses, and the medical image diagnosis apparatuses A1 to AN may be other devices, such as magnetic resonance imaging apparatuses, X-ray diagnosis apparatuses, ultrasound diagnosis apparatuses, PETs (Positron Emission Tomography) or SPECTs (Single Photon Emission Computed Tomography).

The medical information management apparatus 2 is a dedicated or general-purpose computer that functions as a server device of the X-ray CT apparatuses A1 to AN. The medical information management apparatus 2 acquires information on examinations from the X-ray CT apparatuses A1 to AN via the network N. The medical information management apparatus 2 generates proposal information based on the information on examinations and transmits the proposal information to the X-ray CT apparatuses A1 to AN.

The "examinations" herein mean scans (imaging) performed by the medical image diagnosis apparatuses. The "information on examinations" is information on examinations performed using the X-ray CT apparatus and is managed and stored for each patient in the X-ray CT apparatus. As a specific example of the information on examinations, there are examination information, examination results, and information on usage.

The "examination information" means information that is used in a scan (imaging) process, or used in a process on data that is acquired by a scan (imaging) that are performed by the medical image diagnosis apparatus. In other words, the "examination information" is information that is used for examinations and includes, for example, patient information (such as the age, gender, height and weight), information on a region to be scanned (imaged) (such as the head, lungs, chest or abdomen), scan conditions (such as the imaging method, tube current, tube voltage, X-ray tube rotational speed, collection slice thickness, imaging field of view (FOV), and imaging area), and reconstruction conditions (such as the reconstruction method, reconstruction function, reconstruction interval, and reconstruction slice thickness). The "examination results" include raw data that is acquired by imaging in examinations, reconstruction data, and accompanying information that accompanies the raw data and reconstruction data (for example, information, such as examination information and information on the application that is used in each examination). The "information on usage" includes information on the date of each scan that is contained in the accompanying information, such as raw data, information on hardware, such as changes in the temperature of the X-ray tube, reviews from users on options, and pre-post option introduction comparison information.

The "proposal information" is information for proposing an option or upgrade of hardware or software to each of the users of the X-ray CT apparatuses A1 to AN based on the analysis result obtained by analyzing the information on examinations.

The X-ray CT apparatuses A1 to AN are medical image diagnosis apparatuses that are set in hospitals, respectively, and each of which applies X-rays to a patient (subject) and, based on the X-rays having been transmitted through the patient, generates a tomographic image or a three-dimensional image. Multiple X-ray CT apparatuses may be set in the same hospital.

The X-ray CT apparatuses A1 to AN function as client apparatuses of the medical information management apparatus 2 serving as the server device. The X-ray CT apparatuses A1 to AN transmit information on examinations to the medical information management apparatus 2 via the network N. The X-ray CT apparatuses A1 to AN further receives proposal information from the medical information management apparatus 2 and represents the proposal information to the users.

A specific configuration of the X-ray CT apparatus A1 will be described. The configurations of the X-ray CT apparatuses A2 to AN are the same as that of the X-ray CT apparatus A1 and thus description thereof will be omitted.

Figure 2:
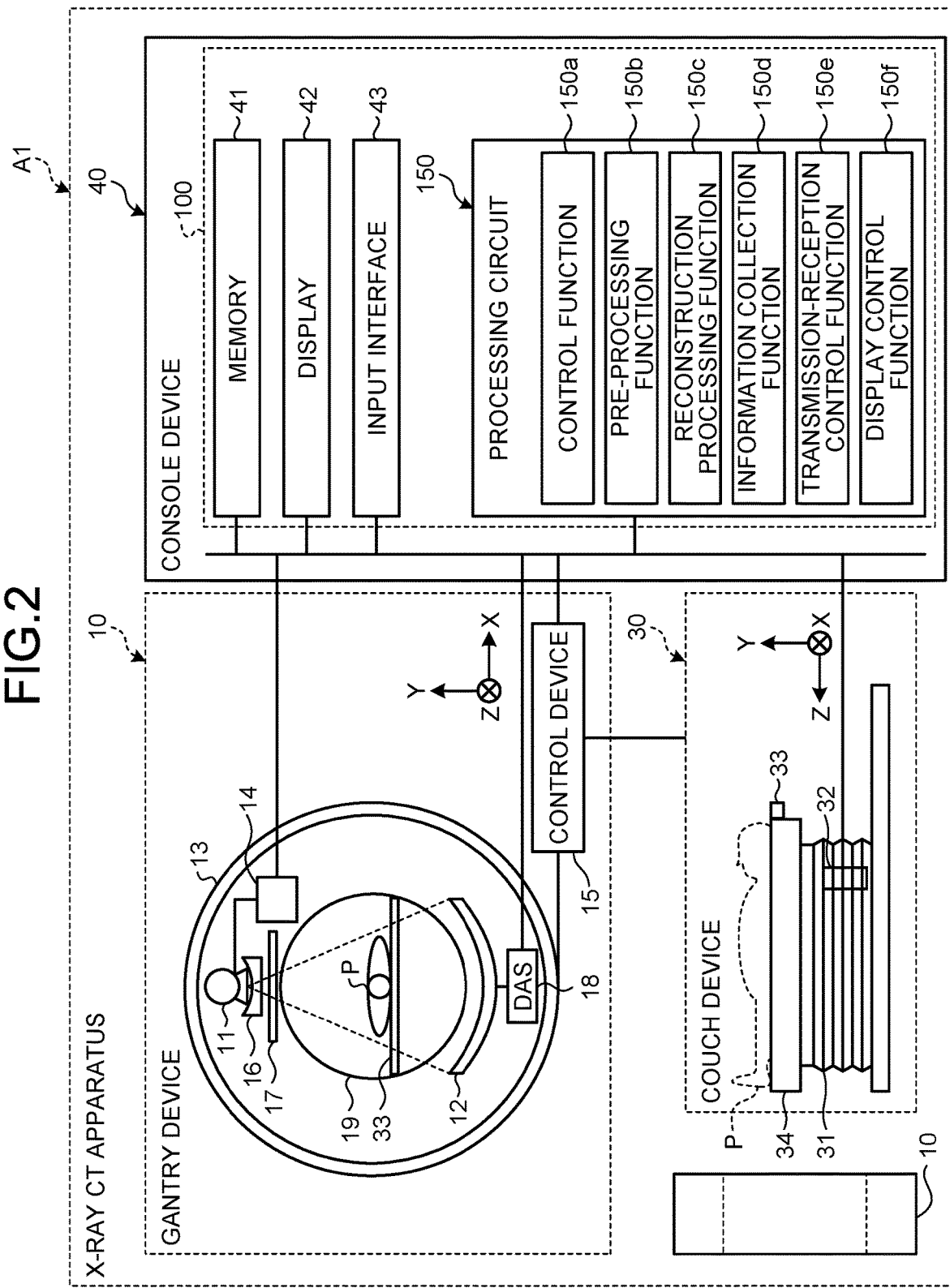
FIG. 2 is a block diagram for explaining an example of a configuration of an X-ray CT apparatus A1.

FIG. 2 is a block diagram for explaining the configuration of the X-ray CT apparatus A1. As illustrated in FIG. 2, the X-ray CT apparatus A1 includes a gantry device 10, a couch device 30, and a console device 40 serving as a terminal device according to the embodiment.

In the first embodiment, a rotation axis of a rotation frame 13 being not tilted or a longitudinal direction of a top board 33 of the couch device 30 is defined as a Z-axis direction, an axis direction orthogonal to the Z-axis direction and is parallel to a floor surface is defined as an X-axis direction, and an axis direction orthogonal to the Z-axis direction and is orthogonal to the floor surface is defined as a Y-axis direction, respectively.

The gantry device 10 includes an imaging system for capturing medical images to be used for diagnosis. In other words, the gantry device 10 is a device that includes the imaging system that applies X-rays to a patient P and collects projection data from data on detection of the X-rays having been transmitted through the subject P and the gantry device 10 includes an X-ray tube 11, a wedge 16, a collimator 17, an X-ray detector 12, an X-ray high voltage device 14, a data acquisition system (DAS) 18, the rotation frame 13, a control device 15, and the couch device 30.

The X-ray tune 11 is a vacuum tube that applies thermal electrons from a cathode (filament) to an anode (target) by application of a high-voltage from the X-ray high voltage device 14.

The wedge 16 is a filter for adjusting the X-ray dosage of the X-rays that are emitted from the X-ray tube 11. Specifically, the wedge 16 is a filter that transmits the X-rays emitted from the X-ray tube 11 and thus attenuates the X-rays such that the X-rays to be applied from the X-ray tube 11 to the subject P are in a predetermined distribution.

The wedge 16 is, for example, a wedge filter or a bow-tie filter that is formed by processing aluminum such that the filter has a given target angle and a given thickness.

The collimator 17 is a lead plate, etc., that narrow down the area irradiated with the X-rays having been transmitted through the wedge 16 and in which a slit is formed by combining multiple lead plates, etc.

The X-ray detector 12 detects the X-rays having emitted from the X-ray tube 11 and having been transmitted through the subject P and outputs an electric signal corresponding to the X-ray dosage to the data collection device (DAS 18). The X-ray detector 12, for example, includes multiple X-ray detection element arrays in which multiple X-ray detection elements are arrayed in a channel direction along an arc about the focal point of the X-ray tube. The X-ray detector 12, for example, has a configuration in which multiple X-ray detection element arrays in each of which multiple X-ray detection elements are arrayed in the channel direction are arrayed in a slice direction (also referred to as the body-axis direction or an array direction).

The X-ray detector 12 is an indirect conversion detector including, for example, a grid, a scintillator array, and an optical sensor array. The scintillator array includes multiple scintillators having scintillator crystals that output light with photon quantities corresponding to the dosage of incident X-ray. The grid includes an X-ray shield that is arranged on the surface of the scintillator array on which X-rays are incident and that has a function of absorbing the scattered X-rays. The optical sensor array has a function of conversion into an electric signal corresponding to the amount of light from the scintillators and includes, for example, an optical sensor, such as a photomultiplier tube (PMT). The X-ray detector 12 may be a direct-conversion detector including a semiconductor element that converts incident X-rays into an electric signal.

The X-ray high voltage device 14 includes a high-voltage generation device that includes an electric circuit of a transformer, a rectifier, etc., and that has a function of generating a high voltage to be applied to the X-ray tube 11 and an X-ray control device that controls an output voltage corresponding to the X-rays that are emitted by the X-ray tube 11. The high-voltage generation device may employ a transformer system or an inverter system. The X-ray high-voltage device 14 may be provided on the rotation frame 13 or may be provided on the side of a fixed frame (not illustrated in the drawing) of the gantry device 10. Note that the fixed frame is a frame that supports the rotation frame rotatably.

The DAS 18 includes an amplifier that perform amplification processing on the electric signal that is output from each X-ray detection element of the X-ray detector 12 and an A/D converter that converts the electric signal into a digital signal and the DAS 18 generates detection data. The detection data that is generated by the DAS 18 is transferred to the console device 40.

The rotation frame 13 is an annular frame that supports the X-ray tube 11 and the X-ray detector 12 such that the X-ray tube 11 and the X-ray detector 12 are opposed to each other and the control device 15 causes the rotation frame 13 to rotate the X-ray tube 11 and the X-ray detector 12. The rotation frame 13 may further support, in addition to the X-ray tube 11 and the X-ray detector 12, the X-ray high-voltage device 14 and the DAS 18. The detection data that is generated by the DAS 18 is, in an example, transmitted from a transmitter that is provided on the rotation frame 13 and that has a light-emitting diode to a receiver that is provided on a non-rotation part of the gantry device 10, such as the fixed frame, and that has a photodiode by optical communication and is then transferred to the console device 40. The method of transmitting the detection data from the rotation frame 13 to the non-rotation part of the gantry device 10 is not limited to optical communication, and the detection data may be transmitted using a non-contact data transmission method or a data transmission method using another system.

The control device 15 includes a processing circuit including a CPU and a drive mechanism, such as a motor and an actuator. The control device 15 has a function of receiving an input signal from an input interface 43 that is attached to the console device 40 or an input interface that is attached to the gantry device 10 and perform operation control on the gantry device 10 and the couch device 30. The control device 15 receives an input signal and performs control of causing the rotation frame 13 to rotate and control of causing the gantry device 10 and the couch device 30 to operate.

For example, based on tilt angle information that is input by the input interface that is attached to the gantry device 10, the control device 15 causes the rotation frame 13 to rotate about an axis parallel with the X-axis direction, thereby tilting the gantry device 10. Note that the control device 15 or a control function 150a that a processing circuit 150 includes is an example of a controller.

The couch device 30 is a device on which the subject P to be scanned is laid and moved and the couch device 30 includes a base 31, a couch drive device 32, the top board 33 and a support frame 34. The base 31 is a casing that supports the support frame 34 movably and perpendicularly. The couch drive device 32 is a motor or an actuator that causes the top board 33 on which the patient P is laid in its longitudinal direction (the Z-axis direction in FIG. 2). The top board 33 that is provided on a top surface of the support frame 34 is a board on which the patient P is laid. The couch drive device 32 may move, in addition to the top board 33, the support frame 34 in the longitudinal direction of the top board 33.

According to a control signal from the control device 15, the couch drive device 32 moves the base 31 vertically. According to a control signal from the control device 15, the couch drive device 32 moves the top board 33 in the longitudinal direction.

The console device 40 is a device that receives an operation of the user on the X-ray CT apparatus A1 and reconstructs X-ray image data from the X-ray detection data that is collected by the gantry device 10. The console device 40 includes a memory 41, a display 42, the input interface 43, and the processing circuit 150.

The medical information processing apparatus 100 according to the embodiment is implemented using, for example, the memory 41, the display 42, the input interface 43, and the processing circuit 150.

The memory 41 is implemented using, for example, a random access memory (RAM), a semiconductor memory device, such as or a flash memory, a hard disk, or an optical disk. The memory 41 stores, for example, projection data (raw data) and CT image data, etc., that are managed for each patient as information on examinations. The memory 41 is an example of a storage.

The memory 41 stores dedicated programs for implementing the control function 150a, a pre-processing function 150b, a reconstruction processing function 150c, an information collection function 150d, a transmission-reception control function 150e, and a display control function 150f.

The display 42 is a monitor that the user refers to and that displays various types of information. For example, the display 42 outputs a medical image (CT image) that is generated by the processing circuit 150 and a graphical user interface (GUI) for receiving various operations from the user. For example, the display 42 is a liquid crystal display or a cathode ray tube (CRT) display. The display 42 is an example of a display unit.

The input interface 43 receives various input operations from the user, converts the received input operations into electric signals, and outputs the electric signals to the processing circuit 150. For example, the input interface 43 receives collection conditions on collecting projection data, reconstruction conditions on reconstructing a CT image, and image processing conditions on generating a post-processing image from a CT image from the user. For example, the input interface 43 is implemented using a mouse and a keyboard, a trackball, a switch, a button, or a joystick. The input interface 43 is an example of an input unit.

The processing circuit 150 controls operations over the X-ray CT apparatus A1. The processing circuit 150 includes, for example, the control function 150a, the pre-processing function 150b, the reconstruction processing function 150c, the information collection function 150d, the transmission-reception control function 150e, and the display control function 150f. In the first embodiment, the respective functions implemented by the control function 150a, the pre-processing function 150b, the reconstruction processing function 150c, the information collection function 150d, the transmission-reception control function 150e, and the display control function 150f are stored in a form of computer-executable programs in the memory 41. The processing circuit 150 is a processor that reads the programs from the memory 41 and executes the programs, thereby implementing the functions corresponding to the respective programs. In other words, the processing circuit 150 having read the respective programs includes the functions that are represented in the processing circuit 150 in FIG. 2.

It has been described that, in FIG. 2, the single processing circuit 150 implements the processing functions that are implemented by the control function 150a, the pre-processing function 150b, the reconstruction processing function 150c, the information collection function 150d, the transmission-reception control function 150e, and the display control function 150f. Alternatively, multiple independent processors may be combined to configure the processing circuit 150 and the respective processors may execute the programs, thereby implementing the functions.

In other words, the above-described respective functions may be configured as programs and a single processing circuit may execute each of the programs or a specific function may be installed in a dedicated and independent program-executable circuit.

Using the control function 150a, the processing circuit 150 controls the various functions of the processing circuit 150 based on input operations that are received from the user via the input interface 43. Using the control function 150a, the processing circuit 150 causes the display 42 to display a high-dose corresponding image and the support information. Using the control function 150a, the processing circuit 150 causes the display 42 to display a measurement tool for setting an area of interest and at least one GUI for executing control based on the support information.

Using the pre-processing function 150b, the processing circuit 150 generates data obtained by performing pre-processing, such as logarithmic transformation and offset processing, sensitivity correction processing between channels, and beam hardening correction, on the detection data that is output from the DAS 18. The data before the pre-processing (detection data) and the data after the pre-processing may be collectively referred to as projection data. Using the reconstruction processing function 150c, the processing circuit 150 generates CT image data by performing reconstruction processing using a filter correction back projection method, a successive approximation reconstruction method, etc.) on the projection data that is generated by the pre-processing function 150b. Using the reconstruction processing function 150c, based on an input operation that is received from the user via the input interface 43, the processing circuit 150 converts the reconstructed CT image data using a known method into tomographic image data or three-dimensional image data on a freely-selected cross section by a known method.

Using the information collection function 150d, the processing circuit 150 collects information on examinations from the memory 41. The information is collected at any set of timing. For example, using the information collection function 150d, the processing circuit 150 collects information on examinations at the timing when image data is stored in the memory 41 after imaging is executed, or at a given time in a day.

Using the transmission-reception control function 150e, the processing circuit 150 transmits the collected information on examinations to the medical information management apparatus 2 via the network N. The information may be transmitted at any set of timing and, for example, using the transmission-reception control function 150e, the processing circuit 150 transmits the information on examinations to the medical information management apparatus 2 via the network N at the timing when the information on examinations is collected or at a given time in a day.

Using the transmission-reception control function 150e, the processing circuit 150 receives proposal information from the medical information management apparatus 2 via the network N. Using the transmission-reception control function 150e, the processing circuit 150 receives an instruction to display the proposal information from the medical information management apparatus 2 via the network N.

Using the display control function 150f, the processing circuit 150 causes the display 42 to display the proposal information that is received from the medical information management apparatus 2.

A configuration of the medical information management apparatus 2 according to the first embodiment will be described.

Figure 3:
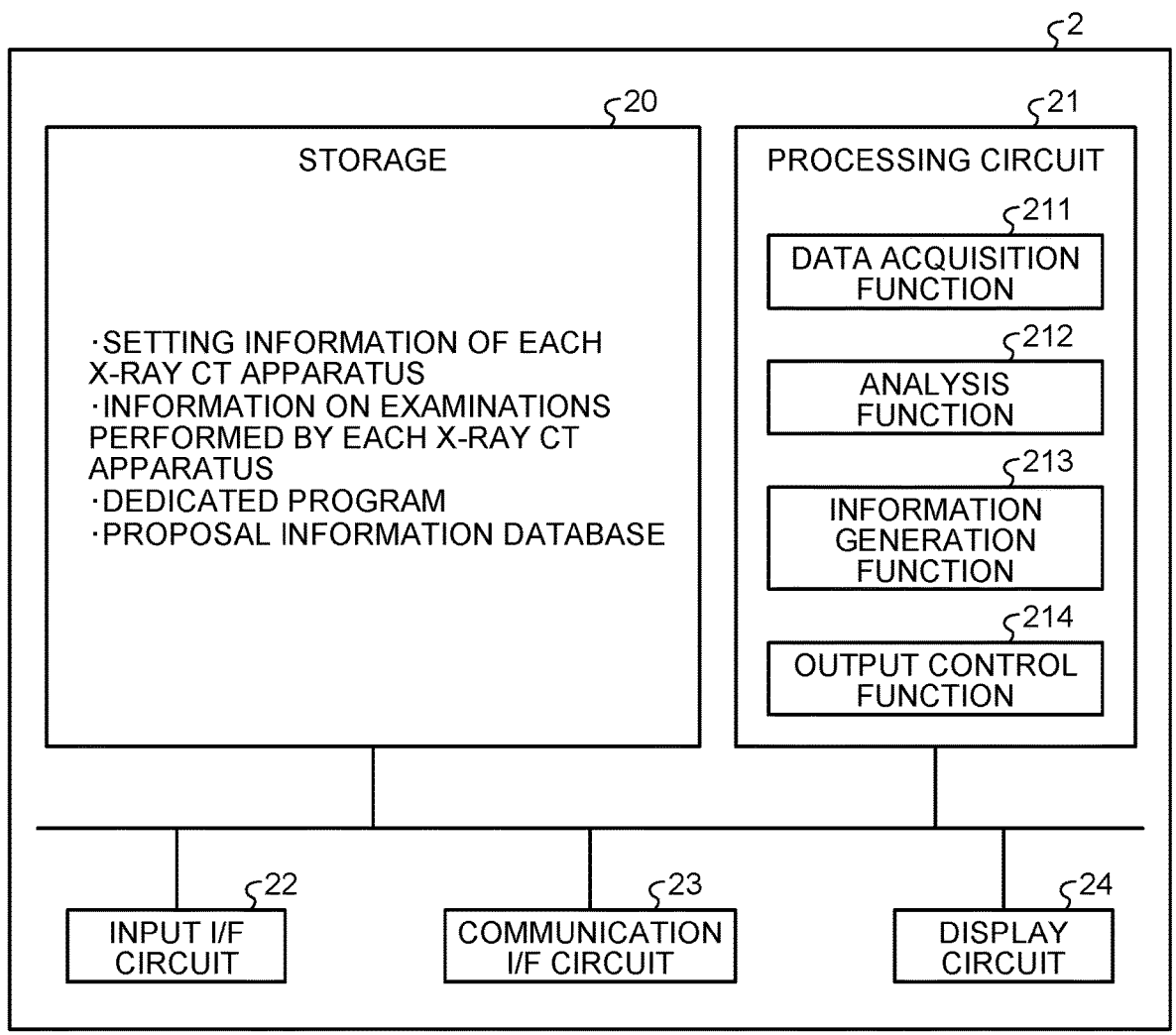
FIG. 3 is a block diagram for explaining an example of a configuration of a medical information management apparatus 2.

FIG. 3 is a block diagram for explaining the configuration of the medical information management apparatus 2. As illustrated in FIG. 3, the medical information management apparatus 2 includes a storage circuit 20, a processing circuit 21, an input I/F circuit 22, a communication I/F circuit 23, and a display circuit 24.

The storage circuit 20 is configured using a RAM, a semiconductor memory device, such as a flash memory, a hard disk or an optical disk. The storage circuit 20 may be configured using a portable medium, such as a USB (Universal Serial Bus) memory or a DVD (Digital Video Disk).

The storage circuit 20 stores dedicated programs (containing, in addition to an application program, an operating system (OS), etc.) for various types of processing that are used in the processing circuit 21, data necessary to execute the programs, volume data, and medical images. Furthermore, the OS may incorporate a GUI that uses a lot of graphics to display information for the operator to the display circuit 24 and that allows basic operations using the input I/F circuit 22.

The storage circuit 20 stores setting information of each of the X-ray CT apparatuses A1 to AN. The "setting information" includes the specification of hardware and software that are installed in the corresponding X-ray CT apparatus and options that are installed. Referring to the setting information makes it possible to know the types, specifications, and versions of the hardware and software that are currently installed in the corresponding X-ray CT apparatus and the time when the hardware and software were installed.

The storage circuit 20 manages and stores information on examinations that is acquired from each of the X-ray CT apparatuses A1 to AN for each apparatus. Furthermore, the storage circuit 20 stores a proposal information database. The "proposal information database" is a table that classifies the proposal information according to the information on examinations and combinations of various keywords contained in a result of analysis to be described below. The proposal information database makes it possible to search the proposal information with keywords.

The processing circuit 21 is a processor that reads the programs from the storage circuit 20 and executes the programs, thereby implementing functions corresponding to the respective programs. The processing circuit 21 includes, for example, a data acquisition function 211, an analysis function 212, an information generation function 213, and an output control function 214. The processing circuit 21 reads the various control programs that are stored in the storage circuit 20 and implements the data acquisition function 211, the analysis function 212, the information generation function 213, and the output control function 214 and generally controls processing operations of the storage circuit 20, the input I/F circuit 22, the communication I/F circuit 23, and the display circuit 24. In other words, the processing circuit 21 having read the respective programs includes the respective functions that are represented in the processing circuit 21 in FIG. 3.

Using the data acquisition function 211, the processing circuit 21 acquires information on examinations from the X-ray CT apparatuses A1 to AN via the network N. The information may be acquired at any set of timing. For example, using the data acquisition function 211, the processing circuit 21 acquires, via the network N, the information on examinations that is transmitted from each of the X-ray CT apparatuses A1 to AN at the timing when the information on examinations is collected. For example, using the data acquisition function 211, the processing circuit 21 acquires the information on examinations at a determined set of timing in a day or a week via the network N. Using the data acquisition function 211, the processing circuit 21 stores the acquired information on examinations in the storage circuit 20.

Using the analysis function 212, the processing circuit 21 analyzes the acquired information on examinations. For example, using the analysis function 212, the processing circuit 21 generates frequency information, or the like, by analyzing the acquired information on examinations based on an analysis item. Using the analysis function 212, the processing circuit 21 compares the frequency information, or the like, with the setting information of each of the X-ray CT apparatuses A1 to AN and determines what proposal information to generate based on the generated frequency information, etc. Furthermore, using the analysis function 212, the processing circuit 21 determines whether to represent a reconstruction image that is generated by background processing performed by each of the X-ray CT apparatuses A1 to AN to the user as proposal information and determines timing of the representation. A specific process performed by the analysis function 212 will be described in detail in each example to be described below.

Using the information generation function 213, the processing circuit 21 generates proposal information according to the result of analysis process that is executed by the analysis function 212. Specifically, using the information generation function 213, the processing circuit 21 generates proposal information by searching the proposal information database using an analysis result obtained by performing the analysis process and a keyword contained in the analysis result, or the like. The information generation function 213 is not limited to one that generates proposal information using the proposal information database. For example, the information generation function 213 may be configured using an AI model in which a keyword that is obtained by the analysis process performed by the analysis function 212 or a combination of keywords serves as an input and the proposal information serves as an output. Such an AI model may be generated, for example, by learning using multiple sets of training data in which a keyword or a combination of keywords serve as an input and corresponding proposal information serves as training data.

Using the information generation function 213, the processing circuit 21 generates CT image data using the raw data contained in the information on examinations by the successive approximation reconstruction method.

Using the output control function 214, the processing circuit 21 transmits the generated proposal information to each of the X-ray CT apparatuses A1 to An via the network N. Using the output control function 214, the processing circuit 21 transmits an instruction to display the proposal information to each of the X-ray CT apparatuses A1 to An via the network N.

It has been described that, in FIG. 3, the processing circuit 21 that is a single processor implements the processing functions that are implemented by the data acquisition function 211, the analysis function 212, the information generation function 213, and the output control function 214. Alternatively, multiple independent processors may be combined to configure the processing circuit and the processors may execute the respective programs, thereby implementing the functions. Furthermore, it has been described that, in FIG. 3, the single storage circuit 20 stores the programs corresponding to the respective functions. Alternatively, a configuration in which a plurality of the storage circuits 20 may be arranged in a distributed manner and the processing circuit 21 reads a corresponding program from the individual storage circuit 20 may be employed.

The input I/F circuit 22 is a circuit to which a signal from an input device, such as a pointing device (such as a mouse) and a keyboard, operable by the operator is input. The input device is incorporated in the input I/F circuit 22 herein. When the operator operates the input device, the input I/F circuit 22 generates an input signal corresponding to the operation and outputs the input signal to the processing circuit 21. The medical information management apparatus 2 may include a touch panel that is formed integrally with the display circuit 24.

The input I/F circuit 22 is not limited to one including a physical operation parts, such as a mouse and a keyboard. For example, examples of the input I/F circuit 22 include an electric signal processing circuit that receives an electric signal corresponding to an input operation from an external input device that is provided independently of the apparatus and that outputs the electric signal to the control circuit.

The communication I/F circuit 23 performs operations of communication with external devices according to given communication standards.

The display circuit 24 is a display that displays an image and the display circuit 24 is configured using a liquid crystal display (LCD), or the like. The display circuit 24 displays various operation screens and various sets of display information, such as image data, on the LCD according to an instruction from the processing circuit 21.

The proposal information generation process performed by the medical system 1 will be described according to typical examples.

Example 1

The system 1 according to Example 1 generates and represents proposal information based on examination information contained in information on examinations.

Figure 4:
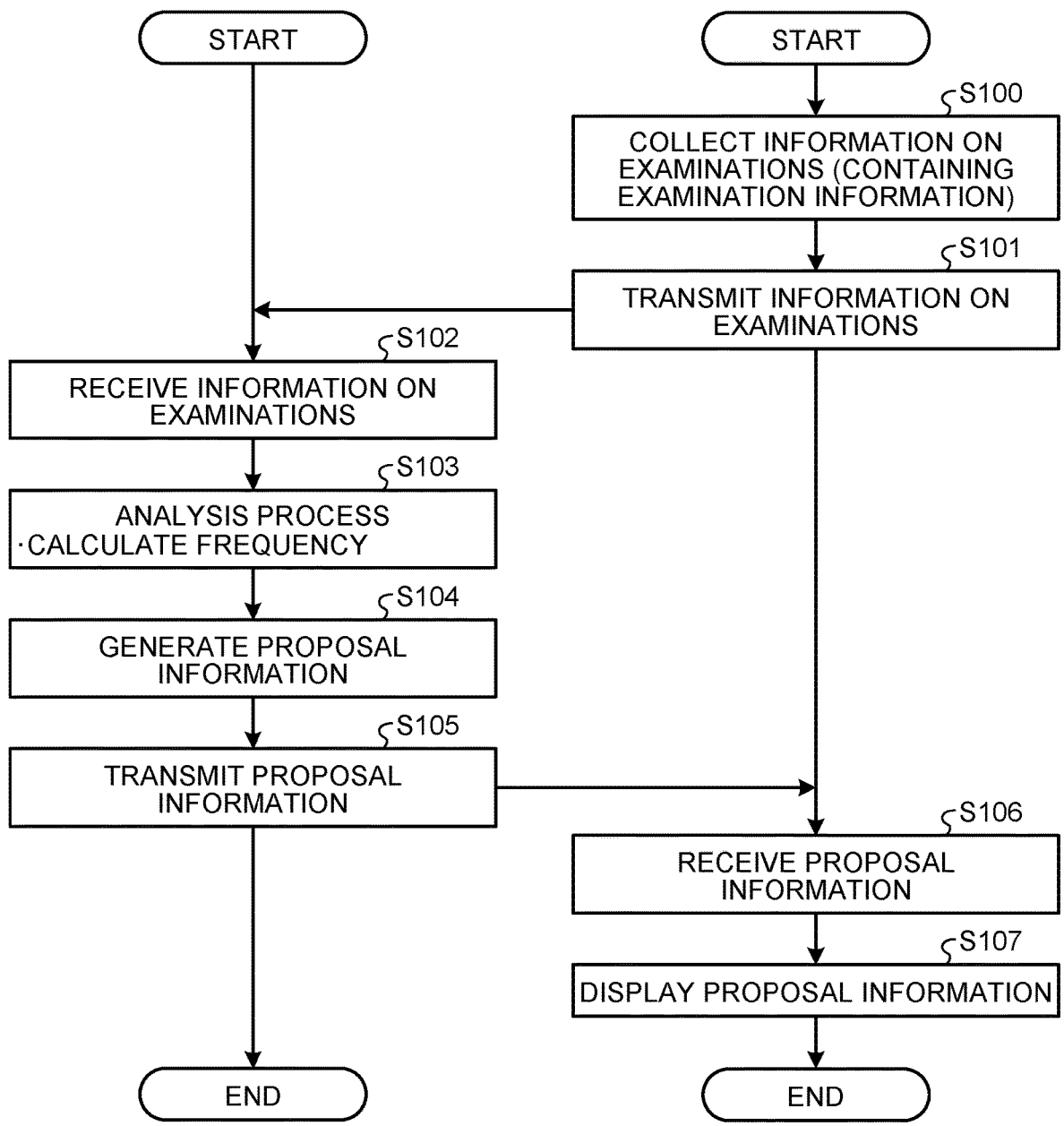
FIG. 4 is a flowchart representing an example of a flow of a proposal information generation process performed by the medical system 1 according to Example 1.

FIG. 4 is a flowchart representing an example of a flow of a proposal information generation process performed by the medical system 1 according to Example 1. Note that, in FIG. 4 and FIGS. 5 to 7, the left row represents a flow of a process performed by the medical information management apparatus 2 and the right row represents a flow of a process performed by the side of the X-ray CT apparatuses that are set in the respective hospitals. In the first embodiment, in order to specify the description, the case in which the right row corresponds to the X-ray CT apparatus A1 is exemplified, and the same process flow applies to other X-ray CT apparatuses A2 to AN and thus description thereof will be omitted.

As illustrated in FIG. 4, using the information collection function 150d, the processing circuit 150 collects information on examinations containing examination information from the memory 41 (step S100). Using the transmission-reception control function 150e, the processing circuit 150 transmits the collected information on examinations to the medical information management apparatus 2 via the network N (step S101).

Using the data acquisition function 211, the processing circuit 21 receives the information on examinations that is transmitted from the X-ray CT apparatus A1 via the network N (step S102).

The processes of steps S100 to S102 are executed repeatedly at timing that is set.

Using the analysis function 212, the processing circuit 21 analyzes the received information on examinations (step S103). For example, using the analysis function 212, the processing circuit 21 analyzes the acquired information on examinations based on an analysis item and generates frequency information. Using the analysis function 212, the processing circuit 21 determines what information to generate based on the generated frequency information.

For example, when the analysis item is the region to be scanned, using the analysis function 212, the processing circuit 21 analyzes the acquired information on examinations and generates, as the frequency information, the number of times each region to be scanned is imaged in a given period in each apparatus. When the frequency is high with respect to the lung zone in the generated frequency information, using the analysis function 212, the processing circuit 21 refers to the setting information of the X-ray CT apparatus A1 and generates proposal information on addition of a lung-zone-related application option that is not set in the X-ray CT apparatus A1.

For example, when the frequency is high with respect to the lung zone in the frequency information and hardware and an application for implementing a lung-zone-related successive approximation reconstruction method are not installed in the X-ray CT apparatus A1, using the analysis function 212, the processing circuit 21 determines to generate proposal information on addition of a lung-zone-related hardware and application option for implementing the successive approximation reconstruction method. Proposal information on addition of multiple hardware and application options may be generated for each region with high frequency.

For example, when the analysis item is the reconstruction condition, using the analysis function 212, the processing circuit 21 analyzes the acquired information on examinations and generates the number of times imaging performed under each reconstruction condition in a given period in each apparatus as frequency information. For example, when the frequency of a specific reconstruction condition is high in the generated frequency information, using the analysis function 212, the processing circuit 21 determines to generate proposal information on addition of an application optimum to the highly-frequent reconstruction condition or an upgrade for optimizing the current application to the highly-frequent reconstruction condition.

For example, when the analysis item is the used application, using the analysis function 212, the processing circuit 21 analyzes the acquired information on examinations and generates the number of times each application is used in a given period in each apparatus as frequency information. When the frequency of a specific application is high in the generated frequency information, using the analysis function 212, the processing circuit 21 refers to the setting information of the X-ray CT apparatus A1 and determines to generate proposal information on addition of a similar application that is not set in the X-ray CT apparatus A1 or on an upgrade of the application. Such proposal information makes it possible to propose the latest algorithm even to the same application.

For example, when the analysis item is the patient age, using the analysis function 212, the processing circuit 21 analyzes the acquired information on examinations and generates the number of examinations according to each age in a given period in each apparatus as frequency information. For example, when the frequency of toddlers is high in the generated frequency information, using the analysis function 212, the processing circuit 21 refers to the setting information of the X-ray CT apparatus A1 and determines to generate proposal information on addition of a toddler fixation tool option that is not set in the X-ray CT apparatus A1.

For example, when the analysis item is the imaging method, using the analysis function 212, the processing circuit 21 analyzes the acquired information on examinations and generates the number of times each imaging method is used in a given period in each apparatus as frequency information. When the frequency of, for example, head-first imaging is high in the generated frequency information, using the analysis function 212, the processing circuit 21 refers to the setting information of the X-ray CT apparatus A1 and determines to generate proposal information on addition of a head rest option that is not set in the X-ray CT apparatus A1. When the frequency of, for example, foot-first imaging is high in the generated frequency information, using the analysis function 212, the processing circuit 21 refers to the setting information of the X-ray CT apparatus A1 and determines to generate proposal information on addition of an foot rest option that is not set in the X-ray CT apparatus A1.

Using the information generation function 213, the processing circuit 21 generates proposal information according to the result of the analysis by the analysis function 212 (step S104). Using the output control function 214, the processing circuit 21 transmits the generated proposal information to the X-ray CT apparatus A1 via the network N (step S105).

Using the transmission-reception control function 150e, the processing circuit 150 receives the proposal information from the medical information management apparatus 2 via the network N (step S106).

Using the display control function 150f, the processing circuit 150 displays the received proposal information on the display 42 (step S107).

As for the mode of displaying the proposal information, there are various methods. For example, the proposal information may be displayed as a pop-up screen or a page dedicated for proposal may be provided. When proposal information on, for example, addition of a lung-zone-related application option is displayed, the proposal information may be displayed during the use of a lung-zone-related application that is currently installed.

Example 2

The medical system 1 according to Example 2 generates proposal information based on an examination result (for example, raw data and CT image data) contained in information on examinations and represents the proposal information.

Figure 5:
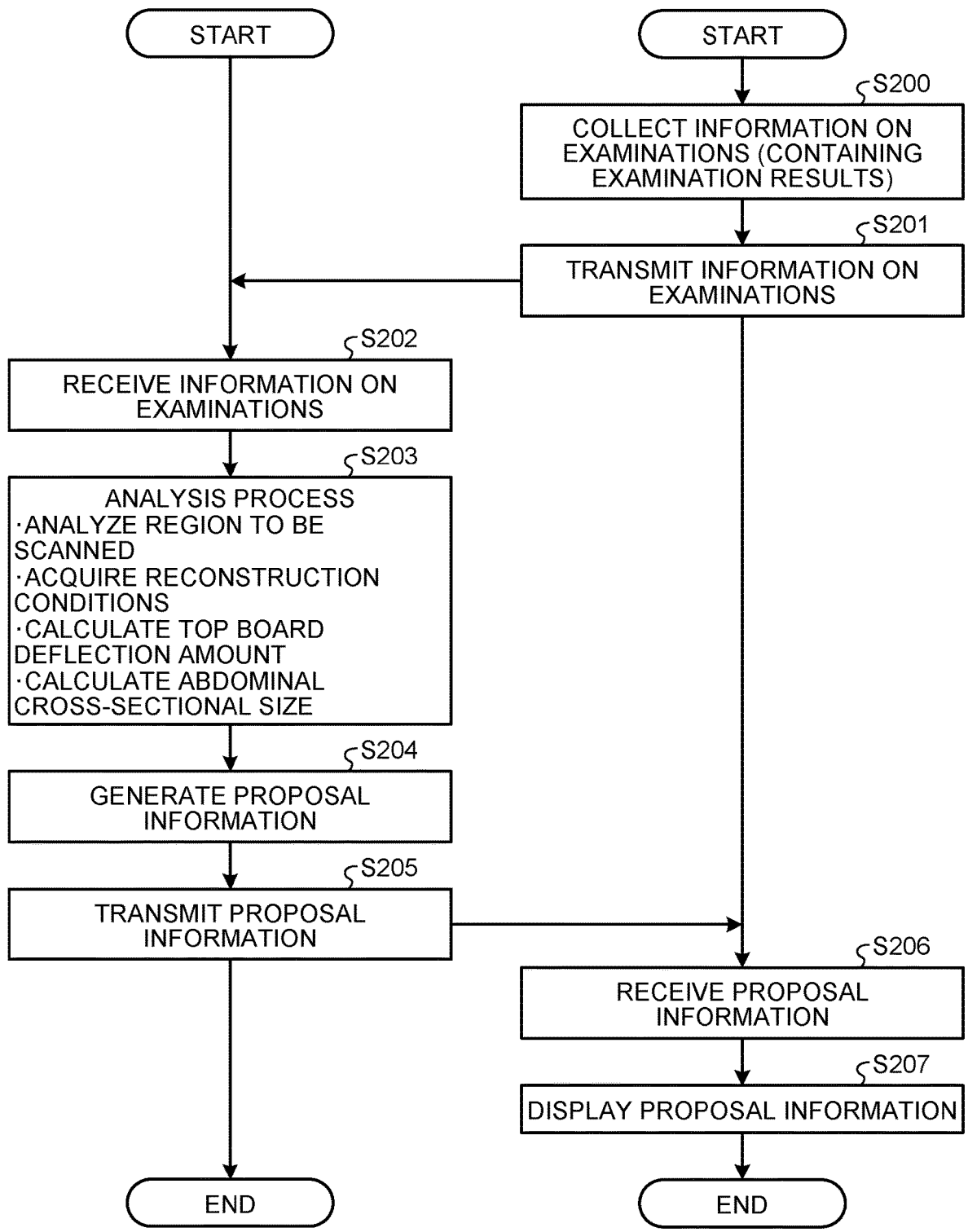
FIG. 5 is a flowchart representing an example of a flow of a proposal information generation process performed by the medical system 1 according to Example 2.

FIG. 5 is a flowchart representing an example of a flow of a proposal information generation process performed by the medical system 1 according to Example 2. The processes of the respective steps S200 to S202 are the same as those of steps S100 to S102 and thus description thereof will be omitted.

Using the analysis function 212, the processing circuit 21 analyzes the received information on examinations (step S203). For example, using the analysis function 212, the processing circuit 21 analyzes the acquired information on examinations based on an analysis item and executes acquisition of a region to be scanned and reconstruction conditions and calculation of a top board deflection amount and an abdominal cross-sectional size, etc. Using the analysis function 212, the processing circuit 21 determines what information to generate based on the site to be scanned, the reconstruction conditions, and the various calculation values that are acquired.

For example, when the analysis item is the reconstruction method, using the analysis function 212, the processing circuit 21 analyzes accompanying information of raw data contained in the acquired information on examinations and acquires a reconstruction method. When the acquired reconstruction method is the filter correction back projection method, using the analysis function 212, the processing circuit 21 refers to the setting information of the X-ray CT apparatus A1 and determines to generate proposal information on addition of a hardware and application option for implementing the successive approximation reconstruction method that is not set in the X-ray CT apparatus A1.

For example, when the analysis item is the top board deflection amount, using the analysis function 212, the processing circuit 21 analyzes a reconstruction image that is contained in the acquired information on examinations and calculates a top board deflection amount. When the calculated top board deflection amount exceeds a tolerance, using the analysis function 212, the processing circuit 21 refers to the setting information of the X-ray CT apparatus A1 and determines to generate proposal information on a couch upgrade that is not set in the X-ray CT apparatus A1.

For example, when the analysis item is the gantry bore diameter, using the analysis function 212, the processing circuit 21 analyzes the reconstruction image that is contained in the acquired information on examinations and calculates a size of a specific area of the patient (for example, an abdominal cross-sectional size). When the calculated abdominal cross-sectional size exceeds the tolerance, using the analysis function 212, the processing circuit 21 refers to the setting information of the X-ray CT apparatus A1 and determines to generate proposal information on an upgrade to a gantry with a large bore diameter that is not set in the X-ray CT apparatus A1.

Using the information generation function 213, the processing circuit 21 generates proposal information according to the result of the analysis by the analysis function 212 (step S204). Particularly, when the analysis item is the reconstruction method, using the information generation function 213, the processing circuit 21 generates a CT image (IR reconstruction image) by executing a successive approximation reconstruction process using the raw data that is contained in the acquired information on examinations and generate proposal information containing the IR reconstruction image. Using the output control function 214, the processing circuit 21 transmits the generated proposal information to the X-ray CT apparatus A1 via the network N (step S205).

Using the transmission-reception control function 150e, the processing circuit 150 receives the proposal information from the medical information management apparatus 2 via the network N (step S206).

Using the display control function 150f, the processing circuit 150 displays the received proposal information on the display 42 (step S207). For example, when the proposal information contains an IR reconstruction image, the IR reconstruction image serving as a sample image and a CT image that is generated by the X-ray CT apparats A1 by performing the filter correction back projection process may be displayed in parallel.

Example 3

When the medical system 1 according to Example 3 generates proposal information based on an examination result (raw data and CT image data) contained in information on examinations and represents the proposal information, the proposal information is generated by the side of the X-ray CT apparatuses. As an assumption of Example 3, the reconstruction processing function 150c of the X-ray CT apparatus A1 is configured to perform the filter correction back projection process and the memory 41 of the X-ray CT apparatus A1 stores a dedicated program for executing the successive approximation reconstruction process that is started as a background according to an instruction from the medical information management apparatus 2.

Figure 6:
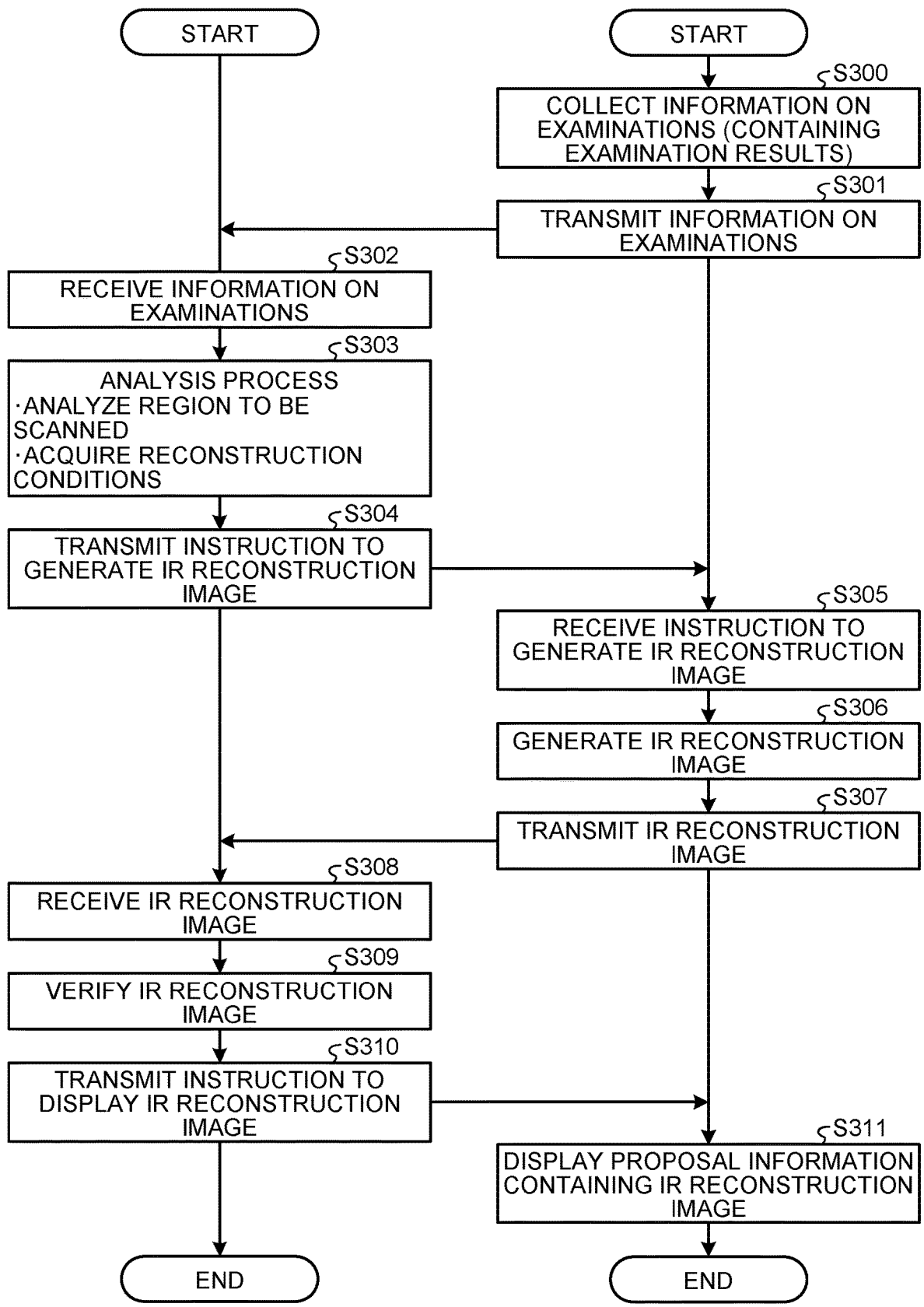
FIG. 6 is a flowchart representing an example of a flow of a proposal information generation process performed by the medical system 1 according to Example 3.

FIG. 6 is a flowchart representing a flow of a proposal information generation process performed by the medical system 1 according to Example 3. The processes of the respective steps S300 to S302 are the same as those of the respective steps S100 to S102 and thus description thereof will be omitted.

Using the analysis function 212, the processing circuit 21 analyzes the received information on examinations (step S303). For example, using the analysis function 212, the processing circuit 21 analyzes the acquired information on examinations based on an analysis item and executes acquisition of a region to be scanned and reconstruction conditions. Using the analysis function 212, the processing circuit 21 determines what presentation information to generate based on the region to be scanned and the reconstruction conditions that are acquired.

For example, when the analysis item is the reconstruction method, using the analysis function 212, the processing circuit 21 analyzes accompanying information of raw data contained in the acquired information on examinations and acquires a reconstruction method. When the acquired reconstruction method is the filter correction back projection method, using the analysis function 212, the processing circuit 21 refers to the setting information of the X-ray CT apparatus A1 and determines to generate proposal information on addition of a hardware and application option for implementing the successive approximation reconstruction method that is not set in the X-ray CT apparatus A1.

Using the information generation function 213, the processing circuit 21 starts the dedicated program for executing the successive approximation reconstruction process that is stored in the memory 41 according to the result of the analysis by the analysis function 212 and generates an instruction to generate an IR reconstruction image. Using the output control function 214, the processing circuit 21 transmits the instruction to generate an IR reconstruction image to the X-ray CT apparatus A1 via the network N (step S304).

Using the transmission-reception control function 150e, the processing circuit 150 receives the instruction to generate an IR reconstruction image from the medical information management apparatus 2 via the network N (step S305).

Using the control function 150a, the processing circuit 150 starts the dedicated program for executing the successive approximation reconstruction process that is stored in the memory 41 in response to the instruction to generate an IR reconstruction image and generates an IR reconstruction image (step S306). Using the transmission-reception control function 150e, the processing circuit 150 transmits the generated IR reconstruction image to the medical information management apparatus 2 via the network N (step S307).

Using the data acquisition function 211, the processing circuit 21 receives the IR reconstruction image that is transmitted from the X-ray CT apparatus A1 via the network N (step S308).

The medical information management apparatus 2 executes verification on the received IR reconstruction image (step S309). The verification determines whether the IR reconstruction image that is generated by the X-ray CT apparatus A1 is adequate to be proposed as a sample image to the user.

For example, using the analysis function 212, the processing circuit 21 executes the verification on the IR reconstruction image by calculating an edge of the received IR reconstruction image and determining whether the result meets a reference value. If necessary, the received IR reconstruction image may be displayed on the display circuit 24 an artificial verification by sight may be performed.

As a result of the verification at step S309, when the IR reconstruction image is adequate as a sample image, using the output control function 214, the processing circuit 21 transmits an instruction to display the IR reconstruction image to the X-ray CT apparatus A1 via the network N (step S310). As a result of the verification at step S309, when the IR reconstruction image is inadequate as a sample image, using the output control function 214, the processing circuit 21 does not transmit the instruction to display the IR reconstruction image.

Using the display control function 150f, the processing circuit 150 displays the IR reconstruction image serving as proposal information on the display 42 in response to the instruction to display the received IR reconstruction image (step S311). The IR reconstruction image serving as a sample image and the CT image that is generated by performing the filter correction back projection process in the X-ray CT apparatus A1 may be displayed in parallel.

Fourth Embodiment

The medical system 1 according to Example 4 generates proposal information based on information on usage that is contained in information on examinations and represents the proposal information.

Figure 7:
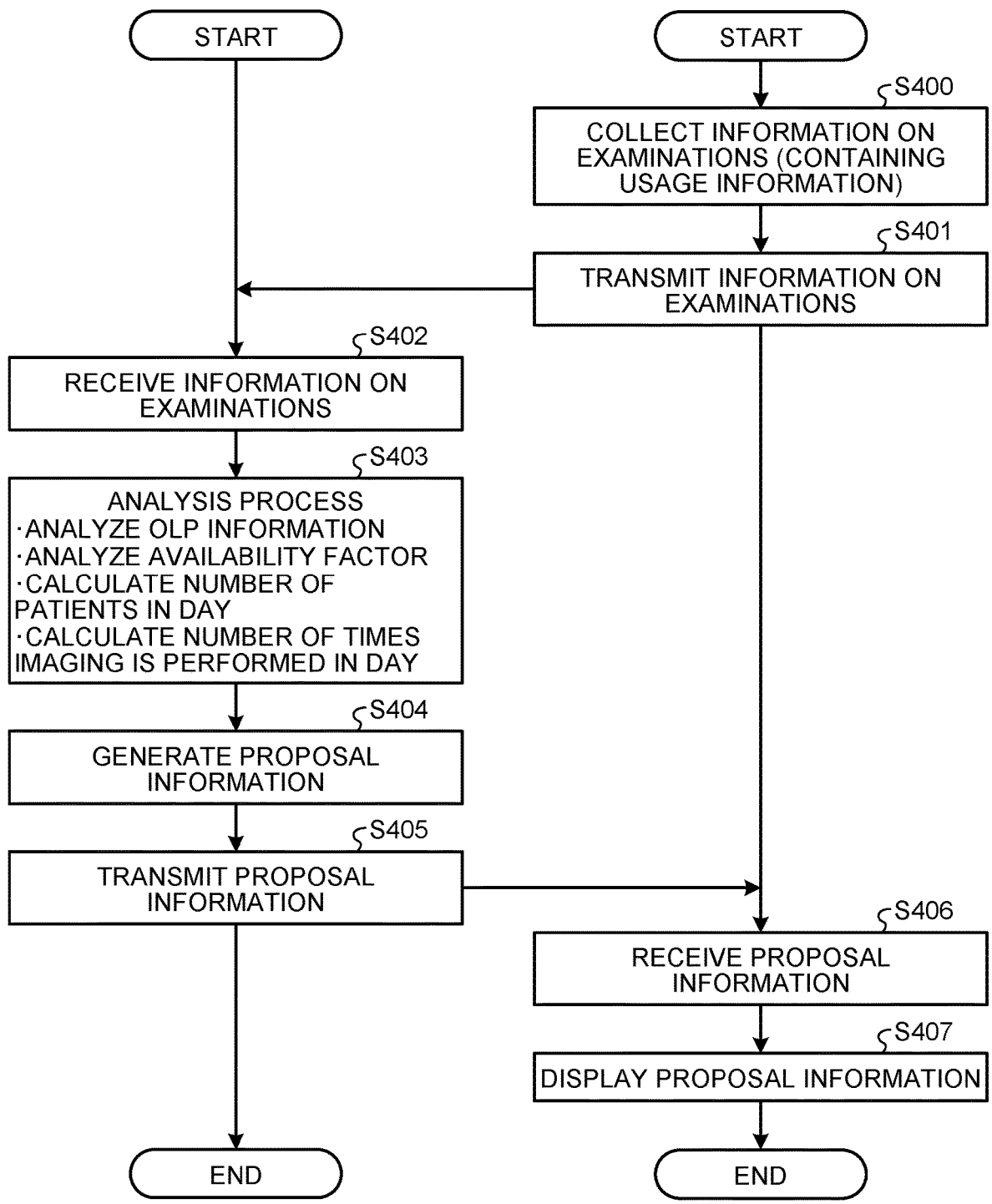
FIG. 7 is a flowchart representing an example of a flow of a proposal information generation process performed by the medical system 1 according to Example 4.

FIG. 7 is a flowchart representing an example of a flow of a proposal information generation process performed by the medical system 1 according to Example 4. The processes of the respective steps S400 to S402 are the same as those of steps S100 to S102 and thus description thereof will be omitted.

Using the analysis function 212, the processing circuit 21 analyzes the received information on examinations (step S403). For example, using the analysis function 212, the processing circuit 21 analyzes the acquired information on examinations based on an analysis item and extracts information on the usage. Using the analysis function 212, the processing circuit 21 determines what proposal information to generate based on the acquired information on the usage.

For example, the case where the analysis item is a tube protection function is assumed. The "tube protection function (overload protection to be referred to as OLP below)" prevents the heat accumulated in the X-ray tube 11 from exceeding a given range based on an amount of heat generated by the X-ray tube and a cooling efficiency by a cooling device to be described below from X-ray generation conditions (the tube voltage, tube current, and X-ray generation time) and the time during which X-ray generation stops (latency time). The OLP controls the timing of X-ray emission by the X-ray tube 11.

Using the analysis function, the processing circuit 21 analyzes changes in the temperature of the X-ray tube over time that are contained in the acquired information on examinations and, for example, calculates a total latency time in a day or an availability factor in a day. When the calculated total latency time in a day is equal to or larger than a reference value or the availability factor in a day is equal to or smaller than a reference value, using the analysis function 212, the processing circuit 21 refers to the setting information of the X-ray CT apparatus A1 and determines to generate proposal information on an X-ray tube upgrade that is not set in the X-ray CT apparatus A1. Upgrading the X-ray tube makes it possible to reduce the amount of heat generation and improve the cooling efficiency by the cooling device. Thus, such proposal information enables specific proposal to shorten the latency time and improve the availability factor to the user.

For example, when the analysis item is the number of times imaging is performed in a day, using the analysis function 212, the processing circuit 21 analyzes the acquired information on examinations and calculates the number of times imaging is performed in a day. When the number of times imaging is performed in a day exceeds a reference value, using the analysis function 212, the processing circuit 21 refers to the setting information of the X-ray CT apparatus A1 and determines to generate proposal information on addition of a raw data saving system option or an increase in the capacity of the storage, such as a disk.

Using the information generation function 213, the processing circuit 21 generates proposal information according to the result of the analysis by the analysis function 212 (step S404). Using the output control function 214, the processing circuit 21 transmits the generated proposal information to the X-ray CT apparatus A1 via the network N (step S405).

Using the transmission-reception control function 150e, the processing circuit 150 receives the proposal information from the medical information management apparatus 2 via the network N (step S406). Using the display control function 150f, the processing circuit 150 displays the received proposal information on the display 42 (step S407).

As described above, the medical system 1 according to the first embodiment is a system in which the medical image diagnosis apparatuses A1 to AN serving as at least one medical image diagnosis apparatus and the medical information management apparatus 2 serving as a server are connected via the network N and the medical system 1 includes the storage circuit 20 serving as a storage, the information generation function 213 serving as a generator, and the display 42 serving as a display unit. The storage circuit 20 stores information on examinations that are performed by the at least one of the X-ray CT apparatuses A1 to AN. The information generation function 213 generates proposal information based on the information on examinations. The display 42 displays the proposal information.

It is thus possible to propose proposal information on addition of an option or an upgrade reflecting the actual examination information, examination results and usage of the X-ray CT apparatuses A1 to AN that are set in the respective hospitals as content unique to each of the X-ray CT apparatuses A1 to AN to each user. As a result, compared to the conventional method, it is possible to realize a proposal of a beneficial option that should be introduced into the medical image diagnosis apparatus, or the like, according to an objective reference.

Second Embodiment

The medical system 1 according to a second embodiment analyzes a trend of options among X-ray CT apparatuses, or the like, using sets of information on examinations that are acquired from the X-ray CT apparatuses A1 to AN, respectively, generates proposal information according to the result of the analysis, and represents the proposal information.

For specific description, in the second embodiment, it is assumed that the X-ray CT apparatuses A1 to AN are set in different hospitals both domestic and overseas. The second embodiment exemplifies the case where sets of information on examinations are acquired from the respective X-ray CT apparatuses A1 to AN and proposal information that is generated using the acquired sets of information on examinations is represented to a user of the X-ray CT apparatus A1.

Figure 8:
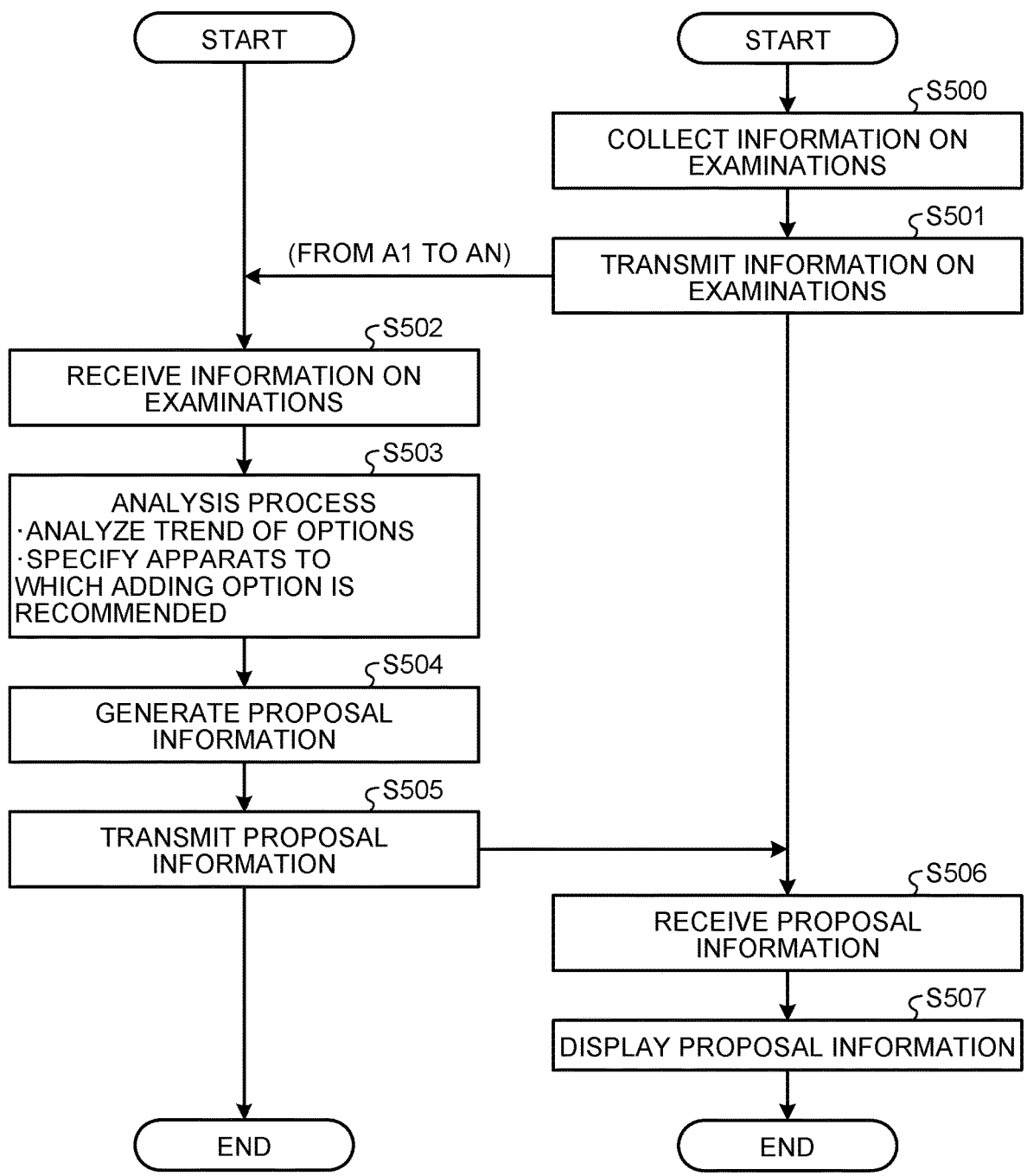
FIG. 8 is a flowchart representing an example of a flow of a proposal information generation process performed by the medical system 1 according to a second embodiment.

FIG. 8 is a flowchart representing an example of a flow of a proposal information generation process performed by the medical system 1 according to the second embodiment. In FIG. 8, the left row represents a flow of a process performed by the medical information management apparatus 2 and the right row represents a flow of a process performed by the side of X-ray CT apparatuses that are set in the respective hospitals.

As illustrated in FIG. 8, using the information collection function 150d, the processing circuit 150 collects information on examinations containing examination information from the memory 41 (step S500). Using the transmission-reception control function 150e, the processing circuit 150 transmits the collected information on examinations to the medical information management apparatus 2 via the network N (step S501). The processes of steps S500 and S501 are executed also by the X-ray CT apparatuses A2 to AN.

Using the data acquisition function 211, the processing circuit 21 receives the sets of information that are transmitted from the X-ray CT apparatuses A1 to AN, respectively, via the network N (step S502).

Note that the processes of steps S500 to S502 are executed repeatedly at timing that is set.

Using the analysis function 212, the processing circuit 21 analyzes the received information on examinations (step S503). For example, using the analysis function 212, the processing circuit 21 analyzes a trend on options using the acquired sets of information on examinations based on an analysis item and extracts information on the trend. Using the analysis function 212, the processing circuit 21 determines what proposal information to generate based on the acquired information on the trend.

For example, the case where the analysis item is options that are introduced during a given period is assumed. In that case, using the analysis function 212, the processing circuit 21 extracts information on addition of options contained in the acquired sets of information on examinations and generates frequency information on each option that is introduced during the given period. Using the analysis function 212, the processing circuit 21 compress the generated frequency information and the setting information of each of the X-ray CT apparatuses A1 to AN and determines an apparatus to which addition of an option is to be proposed.

More specifically, for example, the case where the frequency of addition of an option or an upgrade of the element rows of the detector from 32 rows to 64 rows is high is assumed as the frequency information on each option that is introduced during the given period. In that case, changing the detector from 32 rows to 64 rows can be taken as a trend. Using the analysis function 212, the processing circuit 21 compares the generated frequency information and the setting information of each of the X-ray CT apparatuses A1 to AN and, when the detector including 32 element rows is currently installed in the X-ray CT apparatus A1, determines to provide proposal information inducing addition of a 64-row detector option to the X-ray CT apparatus A1. Note that the proposal information may incorporate, if required, reviews of users who have instructed the 64-row detector, advantages of the 64-row detector, and information on comparison between the 64-row detector and a 32-row detector.

For example, frequency information on each option that is introduced during the given period may be generated according to each country. Incorporating such frequency information according to each country in the proposal information allows the user to know what trend of introduction of options each country has.

The case where the analysis item is reviews on introduced options from each user is assumed. In that case, using the analysis function 212, the processing circuit 21 extracts reviews on options contained in the acquired information on examinations and classifies the reviews according to each of the options. Using the analysis function 212, the processing circuit 21 determines to provide proposal information containing the reviews that are classified according to each of the options to the X-ray CT apparats A1.

Using the information generation function 213, the processing circuit 21 generates proposal information according to the result of the analysis by the analysis function 212 (step S504). Using the output control function 214, the processing circuit 21 transmits the generated proposal information to the X-ray CT apparatus A1 via the network N (step S505).

Using the transmission-reception control function 150e, the processing circuit 150 receives proposal information from the medical information management apparatus 2 via the network N (step S506). Using the display control function 150f, the processing circuit 150 displays the received proposal information on the display 42 (step S507).

The medical system 1 according to the second embodiment provides unified management of the sets of information on examinations that are acquired from the respective X-ray CT apparatuses A1 to AN, analyzes a trend on options among the X-ray CT apparatuses, or the like, generates proposal information according to the result of the analysis and represents the proposal information. It is thus possible to realize proposal of subjective and beneficial option based on the trend in the real market, or the like.

Modification

Each of the above-described embodiments exemplifies the medical system 1 in which the medical information management apparatus 2 and the medical image diagnosis apparatus are independent from each other and communicate with each other via the network. Alternatively, the medical image diagnosis apparatus may incorporate the medical information management apparatus 2 and implement the functions described in each of the embodiments as a stand-alone single apparatus.

The word "processor" used in the description of each of the embodiments means, for example, a central processing unit (CPU), a graphical processing unit (GPU), or a circuit, such as an application specified integrated circuit (ASIC) or a programmable logic device (for example, a simple programmable logic device (SPLD), a complex programmable logic device (CPLD), or a field programmable gate array (FPGA)). The processor reads a program that is saved in the storage circuit 20 or the memory 41 and executes the program, thereby implementing a function. A configuration in which, instead of being saved the program in the storage circuit 20 or the memory 41, the program is directly installed in the circuit of the processor may be employed. In this case, the processor implements the function by reading the program that is incorporated in the circuit.

According to at least one of the above-described embodiments, compared to the conventional method, it is possible to propose an option that should be introduced to the medical image diagnosis apparatus or an upgrade according to an objective reference.

What is claimed is:

1. A medical system in which at least one medical image diagnosis apparatus and a server are connected via a network, the system comprising:
   a storage circuit storing information on examinations that are performed by the at least one medical image diagnosis apparatus;
   a processing circuit configured to generate proposal information based on the stored information on the examinations, the proposal information containing at least one of information for proposing an option and an upgrade to at least one of the medical image diagnosis apparatuses, and information on a trend of options and upgrades; and
   a display circuit configured to display the proposal information.

2. The medical system according to claim 1, wherein the processing circuit is further configured to analyze the information on the examinations.

3. The medical system according to claim 2, wherein the storage circuit further stores information on examinations that are performed by a plurality of the medical image diagnosis apparatuses, and
 the processing circuit is further configured to
  analyze the trend of the options and the upgrades using the information on the examinations.

4. The medical system according to claim 3, wherein the storage circuit further stores information on examinations containing information on X-ray detectors, and
 the processing circuit is further configured to
  analyze a trend of X-ray detector options and upgrades using the information on the examinations, and
  generate the proposal information that proposes at least one of an X-ray detector option and an X-ray detector upgrade based on the trend.

5. The medical system according to claim 2, wherein the storage circuit further stores the information on the examinations containing information on regions to be scanned, and
 the processing circuit is further configured to calculate frequency information on each of the regions to be scanned.

6. The medical system according to claim 5, wherein the processing circuit is further configured to, based on the frequency information on each of the regions to be scanned, generate the proposal information that proposes at least one of an option and an upgrade to at least one of the at least one medical image diagnosis apparatus.

7. The medical system according to claim 2, wherein the storage circuit stores the information on the examinations containing information on patient ages, and
 the processing circuit is further configured to
  calculate frequency information on each of the patient ages, and
  based on the frequency information on each of the patient ages, generate the proposal information that proposes at least one of the option and the upgrade to at least one of the at least one medical image diagnosis apparatus.

8. The medical system according to claim 2, wherein the storage circuit further stores the information on the examinations containing information on imaging methods, and
 the processing circuit is further configured to
  calculate frequency information on each of the imaging methods, and
  based on the frequency information on each of the imaging methods, generate the proposal information that proposes at least any one of the option and the upgrade to at least one of the at least one medical image diagnosis apparatus.

9. The medical system according to claim 2, wherein the storage circuit further stores the information on the examinations containing information on raw data that is acquired by the at least one medical image diagnosis apparatus, and
 the processing circuit is further configured to based on the information on the raw data, generate the proposal information that proposes at least one of the option and the upgrade to at least one of the at least one medical image diagnosis apparatus.

10. The medical system according to claim 9, wherein the processing circuit is further configured to
 generate a first reconstruction image by performing a successive approximation reconstruction process using the information on the raw data, and
 generate the proposal information containing the first reconstruction image.

11. The medical system according to claim 9, wherein the processing circuit is further configured to
 cause at least one of the at least one of the at least one medical image diagnosis apparatus to, based on the information on the raw data, generate a first reconstruction image by performing a successive approximation reconstruction process using the information on the raw data, and
 based on the first reconstruction image, determine whether to cause the display circuit to display the proposal information, and
 the display circuit is further configured to display the proposal information according to a result of the determining by the processing circuit.

12. The medical system according to claim 2, wherein the storage circuit further stores the information on the examinations containing information on image data that is acquired by the at least one medical image diagnosis apparatus, and
 the processing circuit is further configured to
  using the information on the image data, calculate a top board deflection amount, and
  based on the top board deflection amount, generate the proposal information that proposes at least one of a couch option and a couch upgrade to at least any one of the at least one medical image diagnosis apparatus.

13. The medical system according to claim 2, wherein the storage circuit further stores the information on the examinations containing information on image data that is acquired by the at least one medical image diagnosis apparatus, and
 the processing circuit is further configured to
  using the information on the image data, calculate a size of a specific area of a patient, and
  based on the size of the specific area of the patient, generate the proposal information that proposes at least one of a gantry option and a gantry upgrade to at least one of the at least one medical image diagnosis apparatus.

14. The medical system according to claim 2, wherein the storage circuit further stores the information on the examinations containing information on usage of the at least one medical image diagnosis apparatus, and
 the processing circuit is further configured to based on the information on the usage, generate the proposal information that proposes at least one of the option and the upgrade to at least one of the at least one medical image diagnosis apparatus.

15. The medical system according to claim 14, wherein the storage circuit further stores the information on the examinations containing information on an X-ray tube protection function as the information on the usage, and
 the processing circuit is further configured to
  acquire information on a latency time of an X-ray tube in a given period and an availability factor of the X-ray tube, and
  based on the information on the latency time of the X-ray tube and the availability factor, generate the proposal information that proposes at least one of an X-ray tube option and a X-ray tube upgrade to at least any one of the at least one medical image diagnosis apparatus.

16. The medical system according to claim 14, wherein the storage circuit further stores the information on the examinations containing information on a number of times imaging is performed in a given period as the information on the usage, and the processing circuit is further configured to based on the information on the number of times imaging is performed in the given period, generate the proposal information that proposes at least one of a raw data saving system option and a raw data saving system upgrade to at least any one of the at least one medical image diagnosis apparatus.

* * * * *